(12) United States Patent
Gandhi et al.

(10) Patent No.: US 9,345,242 B2
(45) Date of Patent: May 24, 2016

(54) MICROBICIDAL COMPOSITION

(71) Applicants: Dow Global Technologies LLC, Midland, MI (US); Rohm and Haas Company, Philadelphia, PA (US)

(72) Inventors: Usha Gandhi, Hatboro, PA (US); Christine Mcinnis, Blue Bell, PA (US); Paul O. Schook, Lake Zurich, IL (US); Christine M. Schultz, Horsham, PA (US); Terry Michael Williams, Lower Gwynedd, PA (US)

(73) Assignees: Dow Global Technologies LLC, Midland, MI (US); Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/427,004

(22) PCT Filed: Sep. 16, 2013

(86) PCT No.: PCT/US2013/059885
§ 371 (c)(1),
(2) Date: Mar. 10, 2015

(87) PCT Pub. No.: WO2014/046990
PCT Pub. Date: Mar. 27, 2014

(65) Prior Publication Data
US 2015/0230457 A1    Aug. 20, 2015

Related U.S. Application Data

(60) Provisional application No. 61/803,155, filed on Mar. 19, 2013, provisional application No. 61/702,446, filed on Sep. 18, 2012.

(51) Int. Cl.
*A01N 25/30* (2006.01)
*A01N 43/80* (2006.01)

(52) U.S. Cl.
CPC ............... *A01N 25/30* (2013.01); *A01N 43/80* (2013.01)

(58) Field of Classification Search
CPC .................................................. A01N 25/30
USPC .......................................................... 514/372
See application file for complete search history.

(56) References Cited

U.S. PATENT DOCUMENTS

| | | |
|---|---|---|
| 4,295,932 A | 10/1981 | Pocius |
| 5,910,503 A | 6/1999 | Mattox et al. |
| 6,039,965 A | 3/2000 | Donlan et al. |
| 6,139,830 A | 10/2000 | Donlan et al. |
| 2008/0293608 A1 | 11/2008 | Drossmann et al. |
| 2008/0293615 A1 | 11/2008 | Kieffer et al. |
| 2009/0176887 A1 | 7/2009 | Vlasaty et al. |
| 2013/0267570 A1 | 10/2013 | Premachandran et al. |

FOREIGN PATENT DOCUMENTS

| | | |
|---|---|---|
| CA | 1262084 A1 | 10/1989 |
| EP | 1767091 A2 | 3/2007 |
| GB | 2138798 A | 10/1984 |
| WO | 2009041014 A1 | 4/2009 |

*Primary Examiner* — Taofiq A Solola
(74) *Attorney, Agent, or Firm* — Kenneth Crimaldi

(57) ABSTRACT

An aqueous microbicidal composition having two components. The first component is 0.5-5 wt % of a mixture of 5-chloro-2-methyl-4-isothiazolin-3-one and 2-methyl-4-isothiazolin-3-one. The second component is 1-10 wt % of a nonionic surfactant comprising a $C_6$-$C_{12}$ alkyl group, an average of 3-7 moles polymerized units of propylene oxide and an average of 5-12 moles polymerized units of ethylene oxide.

9 Claims, No Drawings

MICROBICIDAL COMPOSITION

This invention relates to microbicidal compositions containing 5-chloro-2-methylisothiazolin-3-one, 2-methylisothiazolin-3-one and a surfactant.

A composition containing 5-chloro-2-methylisothiazolin-3-one, 2-methylisothiazolin-3-one and a nonionic dispersant is disclosed in U.S. Pat. No. 4,295,932. The composition contains a 3:1 mixture of 5-chloro-2-methylisothiazolin-3-one and 2-methylisothiazolin-3-one, and a copolymer of ethylene oxide and propylene oxide which appears to have the same composition as PLURONIC L61 or TERGITOL L61 dispersant. However, there is a need for alternative compositions containing 5-chloro-2-methylisothiazolin-3-one and 2-methylisothiazolin-3-one.

The problem addressed by this invention is to provide alternative compositions containing 5-chloro-2-methylisothiazolin-3-one and 2-methylisothiazolin-3-one.

STATEMENT OF THE INVENTION

The present invention is directed to an aqueous microbicidal composition comprising: (a) 0.5-5 wt % of a mixture of 5-chloro-2-methyl-4-isothiazolin-3-one and 2-methyl-4-isothiazolin-3-one; and (b) 1-10 wt % of a nonionic surfactant comprising a $C_6$-$C_{12}$ alkyl group, an average of 3-7 moles polymerized units of propylene oxide and an average of 5-12 moles polymerized units of ethylene oxide.

The present invention is further directed to a synergistic microbicidal composition comprising: (a) a mixture of 5-chloro-2-methyl-4-isothiazolin-3-one and 2-methyl-4-isothiazolin-3-one; and (b) a nonionic surfactant with structure:

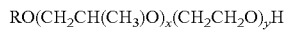

where R is a $C_8$ alkyl group, x is 5 and y is 6 or 9.

The present invention is further directed to an aqueous microbicidal composition comprising: (a) a mixture of 5-chloro-2-methyl-4-isothiazolin-3-one and 2-methyl-4-isothiazolin-3-one; and (b) a nonionic surfactant comprising a $C_6$-$C_{12}$ alkyl group, an average of 3-7 moles polymerized units of propylene oxide and an average of 5-12 moles polymerized units of ethylene oxide; wherein a weight ratio of said nonionic surfactant to said mixture is from 10:1 to 0.8:1.

DETAILED DESCRIPTION OF THE INVENTION

"MIT" is 2-methyl-4-isothiazolin-3-one, also referred to by the name 2-methyl-3-isothiazolone. "CMIT" is 5-chloro-2-methyl-4-isothiazolin-3-one, also referred to by the name 5-chloro-2-methyl-3-isothiazolone. Preferably, the weight ratio of CMIT to MIT is at least 2:1, preferably at least 2.5:1. Preferably, the weight ratio of CMIT to MIT is no greater than 4:1, preferably no greater than 3.5:1. In one preferred embodiment of the invention, the CMIT:MIT ratio is about 3:1.

As used herein, the following terms have the designated definitions, unless the context clearly indicates otherwise. The term "microbicide" refers to a compound capable of inhibiting the growth of or controlling the growth of microorganisms at a locus; microbicides include bactericides, fungicides and algaecides. The term "microorganism" includes, for example, fungi (such as yeast and mold), bacteria and algae. A "solid" composition as the term is used herein is one that is solid at 25° C. The following abbreviations are used throughout the specification: ppm=parts per million by weight (weight/weight), mL=milliliter. Unless otherwise specified, temperatures are in degrees centigrade (° C.), references to percentages are percentages by weight (wt %) and amounts and ratios are on an active ingredient basis, i.e., isothiazolones and nonionic surfactants. Percentages of water in the solid compositions include all water present in any hydrated salts and any free water that may be present.

Preferably, the aqueous composition contains at least 0.8 wt % of a mixture of CMIT and MIT (on an active ingredient basis), preferably at least 1 wt %, preferably at least 1.1 wt % of said mixture, preferably at least 1.2 wt %, preferably at least 1.3 wt %; preferably the composition contains no more than 4.5 wt % of said mixture, preferably no more than 4 wt %, preferably no more than 3.5 wt %, preferably no more than 3 wt %, preferably no more than 2.5 wt %, preferably no more than 2 wt %, preferably no more than 1.8 wt %. Preferably, the weight ratio of nonionic surfactant to CMIT/MIT mixture, based on active ingredient weights of CMIT/MIT and surfactant, is no more than 10:1, preferably no more than 8:1, preferably no more than 6:1, preferably no more than 5:1, preferably no more than 4:1, preferably no more than 3.5:1, preferably no more than 3:1; preferably at least 0.8:1, preferably at least 1:1, preferably at least 1.5:1, preferably at least 2:1, preferably at least 2.5:1, preferably at least 3:1.

A "metal nitrate" preferably is a nitrate salt of an alkali metal, an alkaline earth metal, or ammonium. Preferably, the metal is lithium, sodium, potassium, magnesium, calcium, ammonium, or a combination thereof; more preferably sodium, potassium, magnesium, or combinations thereof. Magnesium is especially preferred.

The aqueous composition preferably contains at least 70 wt % water, preferably at least 80 wt %, preferably at least 85 wt %, preferably at least 87 wt %, preferably at least 89 wt %. Preferably, the aqueous composition contains at least 0.5 wt % of a metal nitrate, preferably at least 1 wt %, preferably at least 1.2 wt %, preferably at least 1.4 wt %, preferably at least 2 wt %; preferably no more than 8 wt %, preferably no more than 6 wt %, preferably no more than 5 wt %, preferably no more than 4 wt %, preferably no more than 3 wt %. Preferably, the aqueous composition contains at least 0.005 wt % of at least one of iodic acid, bromic acid, periodic acid or their salts; preferably at least 0.01 wt %, preferably at least 0.015 wt %, preferably at least 0.02 wt %; preferably no more than 0.2 wt %, preferably no more than 0.1 wt %, preferably no more than 0.05 wt %. Preferably, a copper-based stabilizer may be used including copper nitrate, copper sulfate, or other salts preferably containing at least 0.05 wt %, preferably at least 0.10%, preferably at least 0.15%, preferably at least 0.20%; preferably no more than 2.0%, preferably no more than 1.0%, preferably no more than 5.0

Additionally, peroxide or bronopol based stabilizers may also be used. Typically, the aqueous composition would be diluted for industrial uses to 1.0 to 15 ppm CMIT/MIT (active ingredient basis).

Preferably, the nonionic surfactant has the following structure:

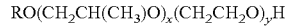

where R is a $C_6$-$C_{12}$ alkyl group, x is from 3-7 and y is from 5-12. The numbers x and y are average values derived from a mixture of compounds. Preferably, R is a $C_6$-$C_{10}$ alkyl group, preferably $C_7$-$C_9$ alkyl group, preferably a $C_8$ alkyl group, preferably a 2-ethylhexyl group. Preferably, R is a branched alkyl group. Preferably, x is 4-6, preferably about 5. Preferably, y is 5-10, preferably 6-10, preferably 6-9, preferably 5-7 or 8-10, preferably 7-10, preferably 8-10, preferably about 9. Preferably, the aqueous composition contains at least 2 wt % of said nonionic surfactant (on an active ingredient basis), preferably at least 3 wt %, preferably at least 3.5 wt %, preferably at least 4 wt %; preferably no more than 9 wt %, preferably no more than 8 wt %, preferably no more than 7 wt %, preferably no more than 6.5 wt %, preferably no more than 6 wt %.

The aqueous composition may contain traces of organic solvents carried over from production of the isothiazolone biocides. Preferably the total level of organic solvents in the aqueous composition is no more than 1%, preferably no more than 0.5%, preferably no more than 0.3%, preferably no more than 0.2%, preferably no more than 0.1%. Typical organic solvents which may be present include, e.g., ethanol, ethyl acetate, acetic acid, butyl acetate, butanol and methylene chloride.

Preferably, the aqueous composition is substantially free of other surfactants, i.e., it contains less than 1 wt % of surfactants other than said nonionic surfactant, preferably less than 0.5 wt %, preferably less than 0.3 wt %, preferably less than 0.2 wt %, preferably less than 0.1 wt %, preferably less than 0.05 wt %.

Preferably, the synergistic microbicidal composition contains: (a) a mixture of 5-chloro-2-methyl-4-isothiazolin-3-one and 2-methyl-4-isothiazolin-3-one; and (b) a nonionic surfactant comprising a $C_8$ alkyl group, an average of 5 polymerized units of propylene oxide and an average of 9 polymerized units of ethylene oxide. Preferably, the weight ratio of said mixture to said nonionic surfactant is from 1:2 to 1:50. Preferably, the synergistic microbicidal composition contains: (a) a mixture of 5-chloro-2-methyl-4-isothiazolin-3-one and 2-methyl-4-isothiazolin-3-one; and (b) a nonionic surfactant comprising a $C_8$ alkyl group, an average of 5 polymerized units of propylene oxide and an average of 6 polymerized units of ethylene oxide. Preferably, the weight ratio of said mixture to said nonionic surfactant is from 1:0.5 to 1:10. Preferably, the nonionic surfactant has the following structure:

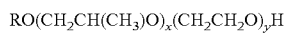

where R is a $C_8$ alkyl group, x is 5 and y is 6 or 9, preferably 9. Preferably the $C_8$ alkyl group is 2-ethylhexyl. The CMIT/MIT mixture (3:1 wt. ratio) was synergistic with a nonionic surfactant of the aforementioned formula in which R is 2-ethylhexyl, x is 5 and y is 9 against *P. aeruginosa*, *E. cloacae* and *K. pnemoniae*; this combination is especially effective in inhibiting growth of *E. cloacae*. The CMIT/MIT mixture (3:1 wt. ratio) was synergistic with a nonionic surfactant of the aforementioned formula in which R is 2-ethylhexyl, x is 5 and y is 6 against *E. cloacae* and *K. pnemoniae*. Preferably, the synergistic microbicidal composition is substantially free of other isothiazolones, i.e., it has less than 1 wt % of isothiazolones other than CMIT/MIT based on total weight of active ingredients, preferably less than 0.5 wt %, preferably less than 0.2 wt %, preferably less than 0.1 wt %. Preferably, the synergistic microbicidal composition is substantially free of other microbicides, i.e., it has less than 1 wt % of microbicides other than CMIT/MIT based on total weight of active ingredients, preferably less than 0.5 wt %, preferably less than 0.2 wt %, preferably less than 0.1 wt %.

The compositions of this invention may contain other ingredients, e.g., defoamers and emulsifiers. The microbicidal compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions onto, into, or at a locus subject to microbial attack. Suitable loci include, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

The specific amount of the microbicidal compositions of this invention necessary to inhibit or control the growth of microorganisms in an application will vary. Typically, the amount of the composition of the present invention is sufficient to control the growth of microorganisms if it provides from 0.1 to 1,000 ppm (parts per million) active ingredients of the composition. It is preferred that the active ingredients (i.e., nonionic surfactant and isothiazolone mixture) of the composition be present in the locus in an amount of at least 1 ppm, preferably at least 5 ppm, preferably at least 10 ppm, preferably at least 20 ppm. It is preferred that the active ingredients of the composition be present in the locus in an amount of no more than 700 ppm, preferably no more than 400 ppm, preferably no more than 200 ppm, preferably no more than 100 ppm, preferably no more than 50 ppm, preferably no more than 30 ppm, preferably no more than 20 ppm.

In industrial and commercial cooling water systems, preferably the total concentration of active ingredients is at least 1 ppm, preferably at least 2 ppm, preferably at least 3 ppm; preferably no more than 25 ppm, preferably no more than 20 ppm, preferably no more than 15 ppm, preferably no more than 12 ppm, preferably no more than 10 ppm, preferably no more than 8 ppm, preferably no more than 6 ppm. In a method of this invention, industrial and commercial cooling water systems are treated by adding, together or separately, the nonionic surfactant and the isothiazolone mixture, in amounts that would produce the concentrations indicated above.

EXAMPLES

Example 1

Compatibility Screening of PLURONIC Surfactants with CMIT/MIT Biocide

A variety of surfactants, including several PLURONIC surfactants, were previously shown to improve the efficacy of low levels of CMIT/MIT (3:1 weight ratio) biocide to control bacterial biofouling on surfaces. In all testing in the present application, CMIT/MIT was free of copper or iodate stabilizers. Biocide and surfactant combinations at 1.5:5 weight percent ratios were effective for controlling biofouling with various organisms at various time points and in different matrices. The PLURONIC and TERGITOL L surfactants are copolymers of propylene oxide (PO) and ethylene oxide (EO), made by capping polypropylene glycols with ethylene oxide. The first digit in the numbering system times 300 gives the molecular weight of the polymerized PO core and the second digit times ten gives the percentage of polymerized ethylene oxide in the surfactant. For example, PLURONIC L61 has a PO core with MW 1800 and is 10% EO overall.

However, using two-part (two drum) treatments for microbial control is undesired as this requires additional pumps, timers, tubing, electricity, inventory, space, and maintenance. The most desired dosing system is a single-product (one-drum) strategy. However, combination formulations must demonstrate excellent compatibility and stability to be viable options.

Stable formulations containing combinations of biocides and surfactants must demonstrate the minimum criteria of good physical and chemical compatibility, especially under storage at elevated temperatures. Minimal to no foaming from the product is also important feature of a combination product.

In this screening study, several PLURONIC surfactants (BASF Co.) were evaluated at 1% and 5% in combination with CMIT/MIT biocide. The physical stability of the biocide with surfactants was evaluated at 40° C. for one week. In this example, the biocide was formulated to a final concentration of 1.5% and was stabilized by 0.15% copper nitrate.

Results of this study showed formulations of PLURONIC L62 (at 1 or 5%) with CMIT/MIT caused phase separation and would therefore be unsuitable for use. Phase separation of CMIT/MIT formulations with PLURONIC L43 was also seen at the 1:1 ratio, but not 1:5 weight ratio. PLURONIC L44, however, showed no phase separation in combination with CMIT/MIT. Based on these screening results, formulations of CMIT/MIT with PLURONIC L44 surfactant would be suitable for further compatibility testing.

| Biocide | Surfactant | Physical Stability Observation after one week at 40° C. | Suitable for Combination Formulations |
|---|---|---|---|
| 1.5% CMIT/MIT | None | No phase separation | NA |
| 1.5% CMIT/MIT | 1% PLURONIC L62 LF | Phase separation | No |
| 1.5% CMIT/MIT | 5% PLURONIC L62 LF | Phase separation | No |
| 1.5% CMIT/MIT | 1% PLURONIC L43 | Phase separation | No |
| 1.5% CMIT/MIT | 5% PLURONIC L43 | No phase separation | Yes |
| 1.5% CMIT/MIT | 1% PLURONIC L44 | No phase separation | Yes |
| 1.5% CMIT/MIT | 5% PLURONIC L44 | No phase separation | Yes |

Example 2

Compatibility of CMIT/MIT Biocide with PLURONIC Surfactants after Extended Heat Aging In this stability/compatibility study, PLURONIC L44 and L44 INH surfactants (BASF Co.) were evaluated at 5% levels in combination with 1.5% levels of CMIT/MIT biocide which was either pre-stabilized or post-stabilized with 0.01% potassium iodate. The physical/chemical stability of the biocide with surfactants was evaluated after storage for 4 weeks at 25° and after 4-8 weeks at 55° C. Suitable formulations would show >90% of each biocide component remaining and no haze or precipitate after 4 weeks of storage at 55° C. A slight color change only is not desired, but is acceptable, as this does not produce solids (precipitate) or affect the concentration of biocide to be dosed. Samples which were unacceptable are highlighted in bold and underlined.

Results of this study showed that CMIT/MIT biocide was not compatible with either PLURONIC L44 or PLURONIC L44 INH surfactants at elevated temperatures (55° C.). More severe degradation of CMIT biocide was seen in samples 1 and 2 (pre-stabilized) vs samples 2 and 3 (post stabilized). All heat aged samples were considered unacceptable due to the loss of biocide (<95% remaining), formation of precipitates, and cloudy appearance. Therefore, CMIT/MIT combinations with PLURONIC L44 or L44 INH surfactants are not robust or compatible under various heat aging conditions and preparation methods.

| Sample | Wt % | wk | °C. | % MIT | % CMIT | % total | % MIT remain | % CMIT remain | appearance |
|---|---|---|---|---|---|---|---|---|---|
| CMIT/MIT pre-stabilized | 10.71% | 0 | 25 | 0.38 | 1.12 | 1.50 | 100% | 100% | clear, colorless |
| PLURONIC L44 INH | 5.00% | 4 | 25 | 0.39 | 1.14 | 1.53 | 103% | 102% | clear, colorless |
| | | 4 | 55 | 0.33 | 0.01 | 0.34 | <u>87%</u> | <u>1%</u> | <u>cloudy, yellow, ppt</u> |
| | | 8 | 55 | 0.24 | 0.01 | 0.25 | <u>63%</u> | <u>1%</u> | <u>cloudy, yellow, ppt</u> |
| CMIT/MIT pre-stabilized | 10.71% | 0 | 25 | 0.38 | 1.12 | 1.50 | 100% | 100% | clear, colorless |
| PLURONIC L44 | 5.00% | 4 | 25 | 0.39 | 1.13 | 1.52 | 103% | 101% | clear, colorless |
| | | 4 | 55 | 0.30 | 0.06 | 0.36 | <u>79%</u> | <u>5%</u> | <u>cloudy, yellow, ppt</u> |
| | | 8 | 55 | 0.24 | 0.05 | 0.29 | <u>63%</u> | <u>4%</u> | <u>cloudy, yellow, ppt</u> |

-continued

| Sample | Wt % | wk | °C. | % MIT | % CMIT | % total | % MIT remain | % CMIT remain | appearance |
|---|---|---|---|---|---|---|---|---|---|
| CMIT/MIT post-stabilized PLURONIC L44 INH | 10.71% | 0 | 25 | 0.36 | 1.06 | 1.4 | 100% | 100% | clear, colorless |
| | 5.00% | 4 | 25 | 0.36 | 1.07 | 1.43 | 100% | 101% | clear, colorless |
| | | 4 | 55 | 0.32 | 0.66 | 0.98 | <u>89%</u> | <u>62%</u> | cloudy, yellow, ppt |
| | | 8 | 55 | 0.28 | 0.26 | 0.54 | <u>78%</u> | <u>25%</u> | cloudy, yellow, ppt |
| CMIT/MIT post-stabilized PLURONIC L44 | 10.71% | 0 | 25 | 0.38 | 1.11 | 1.49 | 100% | 100% | clear, colorless |
| | 5.00% | 4 | 25 | 0.38 | 1.11 | 1.49 | 100% | 100% | clear, colorless |
| | | 4 | 55 | 0.35 | 0.88 | 1.23 | <u>92%</u> | <u>79%</u> | cloudy, yellow, ppt |
| | | 8 | 55 | 0.33 | 0.73 | 1.03 | <u>87%</u> | <u>66%</u> | cloudy, yellow, ppt |

Example 3

Chemical Stability of CMIT/MIT Formulations with Surfactants

Additional studies were done to compare the chemical stability of the CMIT and MIT active ingredients in combination with different surfactants at a (1.5:5 weight ratio) under conditions of extended heat aging.

In this study, several additional surfactants were evaluated at 5% in combination with 1.5% CMIT/MIT biocide which was either pre-stabilized or post-stabilized with 0.01% potassium iodate. The chemical stability of the biocides formulations with the surfactants was evaluated initially at 25° and after 4 and 8 weeks aging at 55° C. Suitable formulations would show >95% of each biocide component remaining and no haze or precipitate after 4 weeks of storage at 55° C. A slight color change only is not desired, but is acceptable, as this does not produce solids (precipitate) or affect the concentration of biocide to be dosed. Samples which were unacceptable are highlighted in bold and underlined.

Combinations of CMIT/MIT with TERGITOL L-64 and Surf. A (2-ethylhexyl with average 5 units PO capped with average 9 units EO) showed very good physical and chemical stability with both isothiazolone biocide actives after 4-8 weeks at 55° C. Only one sample showed significant loss of CMIT after 8 weeks. A slight color was seen with CMIT/MIT plus Surf. A, but no haze or precipitates were observed. Therefore, both of these surfactants would be candidates for robust formulations containing CMIT/MIT biocide.

| Sample | wt % | Wk | °C. | % MIT | % CMIT | total active | % MIT remain. | % CMIT remain | Appear. |
|---|---|---|---|---|---|---|---|---|---|
| CMIT/MIT pre-stabilized TERGITOL L-64 | 10.71 | 0 | 25 | 0.39 | 1.16 | 1.55 | 100% | 100% | clear, colorless |
| | 5.00 | 4 | 55 | 0.38 | 1.15 | 1.54 | 98% | 99% | clear, colorless |
| | | 8 | 55 | 0.39 | 1.07 | 1.46 | 99% | <u>92%</u> | clear, colorless |
| CMIT/MIT post-stabilized TERGITOL L-64 | 10.71 | 0 | 25 | 0.38 | 1.14 | 1.52 | 100% | 100% | clear, colorless |
| | 5.00 | 4 | 55 | 0.37 | 1.09 | 1.47 | 98% | 96% | clear, colorless |
| | | 8 | 55 | 0.38 | 1.10 | 1.49 | 101% | 97% | clear, colorless |
| CMIT/MIT pre-stabilized Surf. A | 10.71 | 0 | 25 | 0.38 | 1.15 | 1.53 | 100% | 100% | clear, colorless |
| | 5.00 | 4 | 55 | 0.40 | 1.18 | 1.58 | 105% | 103% | clear, lt yel |
| | | 8 | 55 | 0.41 | 1.19 | 1.59 | 107% | 103% | clear, lt yel |
| CMIT/MIT post-stabilized Surf. A | 10.71 | 0 | 25 | 0.38 | 1.12 | 1.50 | 100% | 100% | clear, colorless |
| | 5.00 | 4 | 55 | 0.37 | 1.11 | 1.48 | 97% | 99% | clear, lt yel |
| | | 8 | 55 | 0.39 | 1.11 | 1.50 | 102% | 99% | clear, lt yel |

Example 4

Compatibility Screening of CMIT/MIT Formulations with Surf. A, B and C and TERGITOL Surfactants Compatibility screening studies were conducted to evaluate compatibility of CMIT/MIT formulations with various surfactants which had enhanced the efficacy of CMIT/MIT biocide for microbial biofilm control. Physical observations were made with combination formulations containing 1.5% CMIT/MIT biocide with 5% surfactant. The CMIT/MIT biocide was prepared by diluting 14% CMIT/MIT product and post stabilizing with 0.01% potassium iodate (unless noted as not added).

Results showed that CMIT/MIT was physically clear, colorless, and free of precipitates when stabilized with potassium iodate. Removal of the stabilizer in the 1.5% CMIT/MIT formulation caused discoloration and precipitates at 40° and 55° C.

Surf. C (2-ethylhexyl with average 5 units PO capped with average 3 units EO) and TERGITOL L-81 surfactants (with or without CMIT/MIT) were physically unsuitable (cloudy or gelled) at time zero and were not tested further.

Surf. B (2-ethylhexyl with average 5 units PO capped with average 6 units EO) and TERGITOL L-62 showed variable results in combination with CMIT/MIT and would not be considered suitable due to cloudiness, color, or high foam.

Surf. A and TERGITOL L-64 surfactants showed excellent physical properties and compatibility when formulated at 5% with 1.5% CMIT/MIT biocide. These formulations were typically clear, free of cloudiness or color, with minimal to no foaming after short term heat aging up to 55° C.

Example 5

Compatibility and Stability of CMIT/MIT Formulations with Surf. A and TERGITOL L-64 Surfactants after Extended Heat Aging Additional stability testing was conducted on CMIT/MIT formulations containing Surf. B, Surf. A and TERGITOL L-64 surfactants to assess their long term physical and chemical compatibility. Testing was done at 25°, 40°, and 55° C. Results showed that after 2 months, all formulations, except TERGITOL L-64+CMIT/MIT stored at 55° C., showed excellent chemical stability (>95% of initial concentration remaining) and physical appearance (clear, no precipitates or haze). Some light foam and color was observed in the formulations containing Surf. B with CMIT/MIT.

After 3 months of aging, a slight loss of CMIT active (94% remaining) was seen with Surf. A at 55° C. A moderate loss of CMIT (89% remaining) and yellow discoloration was seen with Surf. B at 55° C. All other combinations tested showed excellent physical and chemical compatibility.

After 6 months, all samples aged at room temperature were very stable and physically compatible. As expected, additional loss of biocide at elevated temperatures was noted for some formulations, but for 6 months storage at 40° and 55° C. this is acceptable.

| Surfactant | CMIT/MIT | Time 0 | 4 days at 25° C. | 4 days at 40° C. | 4 days at 55° C. |
|---|---|---|---|---|---|
| None | 1.5% | Clear | Clear | Clear | Clear |
|  | 1.5% no stabilizer | Clear | Clear | Yellow, ppt | Yellow, ppt |
| 5% Surf. C | None | Cloudy | — | — | — |
|  | 1.5% | Cloudy | — | — | — |
| 5% Surf. B | None | Clear | Clear, high foam | Cloudy, white | Cloudy, white |
|  | 1.5% | Clear | Clear, high foam | Clear, sl foam | Cloudy, white, sl foam |
| 5% Surf. A | None | Clear | Clear, med foam | Clear Sl foam | Clear, sl foam |
|  | 1.5% | Clear | Clear, med foam | Clear | Clear |
| 5% TERGITOL L-62 | None | Clear | Clear, low foam | Clear | Cloudy |
|  | 1.5% | Clear | Clear, low foam | Clear | Cloudy, sl yellowing |
| 5% TERGITOL L-64 | None | Clear | Clear | Clear | Clear |
|  | 1.5% | Clear | Clear | Clear | Clear |
| 5% TERGITOL L-81 | None | Cloudy, gelled, phase separation | — | — | — |
|  | 1.5% | Cloudy, gelled, phase separation | — | — | — |

Biocide Stability and Compatibility at 2 Months Storage

| Sample | % CMIT | % MIT | Total % Active | % CMIT Remain | % MIT Remain | Appearance |
|---|---|---|---|---|---|---|
| Surf. A + CMIT/MIT 25° C. | 1.134 | 0.375 | 1.51 | 101% | 101% | Clear |
| Surf. A + CMIT/MIT 40° C. | 1.140 | 0.374 | 1.51 | 101% | 101% | Clear |
| Surf. A + CMIT/MIT 55° C. | 1.075 | 0.373 | 1.45 | 95% | 101% | Clear |
| TERGITOL L-64 + CMIT/MIT 25° C. | 1.132 | 0.374 | 1.51 | 101% | 102% | Clear |
| TERGITOL L-64 + CMIT/MIT 40° C. | 1.123 | 0.372 | 1.49 | 101% | 102% | Clear |
| TERGITOL L-64 + CMIT/MIT 55° C. | 0.174 | 0.251 | 0.43 | __16%__ | 69% | Yellow ppt |
| CMIT/MIT 25° C. | 1.217 | 0.403 | 1.62 | 105% | 105% | Clear |
| CMIT/MIT 40° C. | 1.186 | 0.392 | 1.58 | 102% | 102% | Clear |
| CMIT/MIT 55° C. | 1.185 | 0.392 | 1.58 | 102% | 102% | Clear |
| Surf. B + CMIT/MIT 25° C. | 1.131 | 0.374 | 1.51 | 100% | 100% | Clear, foam |
| Surf. B + CMIT/MIT 40° C. | 1.140 | 0.376 | 1.52 | 101% | 100% | Pale yellow, Foam |
| Surf. B + CMIT/MIT 55° C. | 1.081 | 0.376 | 1.46 | 95% | 100% | Clear, foam |

Surf. A + CMIT/MIT Initial concentrations = 1.133% CMIT + 0.375% MIT
Surf. A + CMIT/MIT Initial concentrations = 1.127% CMIT + 0.371% MIT
TERGITOL L-64 + CMIT/MIT Initial concentrations = 1.116% CMIT + 0.365% MIT
CMIT/MIT initial concentration = 1.163% CMIT + 0.384% MIT Biocide Stability and Compatibility at 3 Months Storage

| Sample | % CMIT | % MIT | Total % Active | % CMIT Remain | % MIT Remain | appearance |
|---|---|---|---|---|---|---|
| Surf. A + CMIT/MIT 25° C. | 1.137 | 0.378 | 1.51 | 101% | 102% | Clear |
| Surf. A + CMIT/MIT 40° C. | 1.113 | 0.367 | 1.48 | 99% | 99% | Clear |
| Surf. A + CMIT/MIT 55° C. | 1.057 | 0.361 | 1.42 | __94%__ | 97% | Clear |
| TERGITOL L-64 + CMIT/MIT 25° C. | 1.121 | 0.370 | 1.49 | 100% | 101% | Clear |
| TERGITOL L-64 + CMIT/MIT 40° C. | 1.091 | 0.364 | 1.46 | 98% | 100% | Clear |
| TERGITOL L-64 + CMIT/MIT 55° C. | nt | nt | nt | Nt | nt | Nt |
| CMIT/MIT 25° C. | 1.212 | 0.401 | 1.61 | 104% | 104% | Clear |
| CMIT/MIT 40° C. | 1.184 | 0.391 | 1.58 | 102% | 102% | Clear |
| CMIT/MIT 55° C. | 1.212 | 0.414 | 1.63 | 104% | 108% | Clear, pale yellow |
| Surf. B + CMIT/MIT 25° C. | 1.126 | 0.372 | 1.50 | 99% | 99% | Clear, |
| Surf. B + CMIT/MIT 40° C. | 1.131 | 0.374 | 1.50 | 100% | 100% | Pale yellow, foam |
| Surf. B + CMIT/MIT 55° C. | 1.008 | 0.399 | 1.41 | __89%__ | 106% | Yellow |

Biocide Stability and Compatibility at 6 Months Storage

| Sample | % CMIT | % MIT | Total % Active | % CMIT Remain | % MIT Remain | Appearance |
|---|---|---|---|---|---|---|
| Surf. A + CMIT/MIT 25° C. | 1.152 | 0.382 | 1.53 | 102% | 103% | Clear |
| Surf. A + CMIT/MIT 40° C. | 1.085 | 0.360 | 1.44 | 96% | 97% | Clear |
| Surf. A + CMIT/MIT 55° C. | 0.922 | 0.357 | 1.28 | __82%__ | 96% | Pale yellow |
| TERGITOL L-64 + CMIT/MIT 25° C. | 1.134 | 0.375 | 1.51 | 102% | 103% | Clear |
| TERGITOL L-64 + CMIT/MIT 40° C. | 0.974 | 0.365 | 1.34 | __87%__ | 100% | Clear |
| TERGITOL L-64 + CMIT/MIT 55° C. | nt | nt | nt | nt | Nt | Nt |
| CMIT/MIT 25° C. | 1.239 | 0.414 | 1.65 | 107% | 108% | Clear |
| CMIT/MIT 40° C. | 1.226 | 0.394 | 1.62 | 105% | 103% | Clear |

-continued

| Sample | % CMIT | % MIT | Total % Active | % CMIT Remain | % MIT Remain | Appearance |
|---|---|---|---|---|---|---|
| CMIT/MIT 55° C. | 1.235 | 0.442 | 1.68 | 106% | 115% | Clear |
| Surf. B + CMIT/MIT 25° C. | 1.147 | 0.378 | 1.53 | 101% | 101% | Clear, foam |
| Surf. B + CMIT/MIT 40° C. | 1.105 | 0.369 | 1.47 | 98% | 99% | Pale yellow, foam |
| Surf. B + CMIT/MIT 55° C. | nt | nt | nt | nt | nt | Nt |

Synergy Testing with Planktonic Bacteria

High Resolution Minimum Inhibitory Concentration (HR-MIC) studies were conducted to determine the inhibitory levels of CMIT/MIT biocide and surfactants, both alone and in combination. Testing was done in standard lab media. Results were determined after 24 hours incubation at 30° C.

Materials and Methods

The synergism of the combination of the present invention was demonstrated by testing a wide range of concentrations and ratios of the compounds. One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$Q_a/Q_A + Q_b/Q_B$ = Synergy Index ("SI") wherein:

$Q_A$ = concentration of compound A (first component) in ppm, acting alone, which produced an end point (MIC or MBC of Compound A).

$Q_a$ = concentration of compound A in ppm, in the mixture, which produced an end point.

$Q_B$ = concentration of compound B (second component) in ppm, acting alone, which produced an end point (MIC or MBC of Compound B).

$Q_b$ = concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms.

The tests were set up with 96-well microtiter plate using the BIOMEK 2000 Workstation employing a high resolution MIC combination test method, which provides multiple combinations of two biocides in one test plate. The lowest concentration of the biocide where no growth (inhibition) was observed in the mineral salts plus glucose-yeast extract (M9GY) medium was defined as the minimum inhibitory concentrations (MIC) of the combination.

A 1:20 dilution of a 24 hour old culture of *Pseudomonas aeruginosa* (ATTCC 15442), *Enterobacter cloacae* (ATCC 13047), or *Klebsiella pneumoniae* (ATCC 10031) was used for testing. Each well of the microtiter plate received 20 μl of the pure culture suspension of each organism at a final density of $10^6$ colony forming units (CFU) per ml.

MIC plates were incubated at 30° C. for 24 hours and were inspected visually for the presence or absence of microbial growth (turbidity). Tests were set up in duplicate with different starting concentrations of biocides to increase the number of possible combinations displaying antimicrobial activity. The lowest concentration of biocide that inhibited growth was recorded as the MIC. All biocide results are reported on an active ingredient basis in ppm (parts per million).

Results showed that CMIT/MIT was synergistic with Surf. A and Surf. B. Synergy index values are summarized in the following table. The surfactants alone showed no antibacterial activity at 10,000 ppm.

Synergy with CMIT/MIT and Surf. A was observed against all three bacterial strains tested. Surf. B only demonstrated synergy with CMIT/MIT against the Enterobacter and Klebsiella strains, not against *Pseudomonas aeruginosa*.

Summary of synergy results with CMIT/MIT biocide and Surf. A or Surf. B

| Surfactant | Synergy Index Value Range | Synergistic Ratios (Biocide:Surfactant) | Bacterial Strains with Synergy Observed |
|---|---|---|---|
| Surf. A | 0.50 to 0.83 | 1/50 to 1/2 | P. aeruginosa E. cloacae K. pnemoniae |
| Surf. B | 0.50 to 0.67 | 1/10 to 1/0.5 | E. cloacae K. pnemoniae |

Synergy with Surf. A and CMIT/MIT Biocide.

| Microorganism | $Q_a$ ppm CMIT/MIT | $Q_b$ ppm Surf. A | Synergy Index Values | Synergy Value Ratios (CMIT/MIT:Surf. A) |
|---|---|---|---|---|
| P aeruginosa Expt. 1 | 2 | 0 | 1.0 | — |
|  | 1 | 10 | 0.50 | 1/10 |
|  | 1 | 15 | 0.50 | 1/15 |
|  | 0 | >10,000 | 1.0 | — |
| E. cloacae Expt. 1 | 1 | 0 | 1.0 | — |
|  | 0.8 | 5 | 0.80 | 1/6.3 |
|  | 0.8 | 10 | 0.80 | 1/12.5 |
|  | 0.5 | 15 | 0.50 | 1/30 |
|  | 0.5 | 20 | 0.50 | 1/40 |
|  | 0.5 | 25 | 0.50 | 1/50 |
|  | 0 | >10,000 | 1.0 | — |
| K pneumoniae Expt. 1 | 1 | 0 | 1.0 | — |
|  | 0.8 | 5 | 0.80 | 1/6 |
|  | 0.8 | 10 | 0.80 | 1/13 |
|  | 0.8 | 15 | 0.80 | 1/19 |
|  | 0.8 | 20 | 0.80 | 1/25 |
|  | 0.8 | 25 | 0.80 | 1/31 |
|  | 0 | >10,000 | 1.0 | — |
| P aeruginosa Expt. 2 | 2 | 0 | 1.0 | — |
|  | 1 | 4 | 0.50 | 1/4 |
|  | 1 | 10 | 0.50 | 1/10 |
|  | 0 | >10,000 | 1.0 | — |
| E. cloacae Expt. 2 | 0.6 | 0 | 1.0 | — |
|  | 0.5 | 1 | 0.83 | 1/2 |
|  | 0.5 | 2 | 0.83 | 1/4 |
|  | 0.5 | 6 | 0.83 | 1/6 |
|  | 0 | >10,000 | 1.0 | — |
| K pneumoniae Expt. 2 | 1 | 0 | 1.0 | — |
|  | 0.8 | 2 | 0.8 | 1/2.5 |
|  | 0.8 | 4 | 0.8 | 1/5 |
|  | 0 | >10,000 | 1.0 | — |

Synergy with Surf. B and CMIT/MIT Biocide.

| Microorganism | $Q_a$ ppm CMIT/MIT | $Q_b$ ppm Surf. B | Synergy Index Values | Synergy Value Ratios (CMIT/MIT:Surf. B) |
|---|---|---|---|---|
| P aeruginosa | 2 | 0 | 1.0 | — |
| Expt 1 | 2 | >10,000 | 1.0 | No synergy |
|  | 0 | >10,000 | 1.0 | — |
| E. cloacae | 3 | 0 | 1.0 | — |
| Expt 1 | 2 | 4 | 0.67 | 1/2 |
|  | 2 | 2 | 0.67 | 1/1 |
|  | 2 | 1 | 0.67 | 1/0.5 |
|  | 0 | >10,000 | 1.0 | — |
| K. pneumoniae | 2 | 0 | 1.0 | — |
| Expt 1 | 1 | 6 | 0.5 | 1/6 |
|  | 1 | 8 | 0.5 | 1/8 |
|  | 1 | 10 | 0.5 | 1/10 |
|  | 0 | >10,000 | 1.0 | — |

Biofilm control studies with CMITIMIT Biocide Plus Surfactants.
Materials and Methods A model biofilm system was used to evaluate the efficacy of CMIT/MIT biocide and surfactant treatments (alone and in combination) for eradication of established biofilms. The system involved growing biofilms on a glass microscope slide in a phosphate-buffered saline solution (100 ml) with 1% trypticase soy broth. A mixture of three bacteria (*Pseudomonas aeruginosa* ATTCC 15442, *Enterobacter cloacae* ATCC 13047, and *Klebsiella pneumoniae* ATCC 10031) was used as the inocula for the biofilm samples. After 24-48 hrs incubation with agitation (150-200 rpm) at 30° C. the pre-grown biofilm slides were rinsed in phosphate buffered-saline and transferred to biocide-treated contact solutions containing synthetic cooling water (584 mg/l $CaCl_2$-$2H_2O$), 203 mg/l $MgCl_2$-$6H_2O$), 84 mg/l $NaHCO_3$, 5 mg/l acrylate polymer, and 0.1% trypticase soy broth). After a defined contact period (4-24 hr), biofilms were rinsed, scraped and viable counts of surviving bacteria were determined by plate counting or MPN using trypticase soy broth (TSB) medium.

Data are provided below to demonstrate the added efficacy of CMIT/MIT biocide in the presence of surfactants to control bacterial fouling. Addition of the surfactants alone showed no biofilm control even at elevated concentrations. Therefore, the surfactants demonstrated a synergistic effect with CMIT/MIT in controlling bacterial fouling on surfaces. In general an increase in the log reduction of at least 0.5 log units versus the control or another treatment is evidence of a measurable improvement.

For the CDC Biofilm Reactor studies, a CDC Biofilm Reactor was used according to the procedure of ASTM E2562-07, with the following exceptions:

1. Bacterial species altered from *P. aeruginosa* to include *Legionella pneumophila* TCC BAA74, *Legionella*-host organism Acanthamoeba polyphaga ATCC 30461, and undefined environmental bacterial organisms. The environmental organisms and *Legionella* were derived from cell-suspensions.
2. Batch phase (incubation without flow) extended past 24 hours to 5 days to support the slower growth rate of *Legionella*
3. To reflect conditions relevant to cooling tower environments, the media was changed to synthetic cooling water and a slower rate of media flow was used to reflect slower *Legionella* growth rate.
4. The treatment protocol also included the addition of a 24 hour post-treatment flush with BCDMH-halogenated water (0.6 ppm available chlorine) to detect how targeted biocides affect viable attached biofilms to coupons with a realistic maintenance dosing added after initial dosing.
5. Sampling has been altered, removing the pre-sampling rinse step and with steps 10.3.4-10.4.2 removed and replaced with a vigorous vortexing step to remove biofilms from the coupons tested. *Legionella* counts not duplicate plated.

Example 6

CMIT/MIT biocide (1.5 ppm active ingredient; a.i.) alone showed a 2.3 log reduction at 4 hours and a 0.7 log reduction at 24 hours for control of bacterial biofouling compared to the untreated control. Surf. A, B and C tested alone at 15 ppm active showed no decrease in bacterial fouling on surfaces compared to the untreated control. The combinations of CMIT/MIT with Surf. A, B, or C (1:10 wt % ratio) all showed improved bacterial biofilm control compared to the CMIT/MIT treatment alone. Therefore, these surfactants improved the control of bacterial biofilm growth by CMIT/MIT biocide, yet showed no control when tested alone.

| Treatment | Sample Time | Biofilm Log Growth Cells/$cm^2$ | Log Reduction vs Untreated Control |
|---|---|---|---|
| Untreated Control | 4 hour | 6.2 | 0.0 |
|  | 24 hour | 6.8 | 0.0 |
| 1.5 ppm a.i. CMIT/MIT | 4 hour | 4.0 | 2.3 |
|  | 24 hour | 5.1 | 1.7 |
| 15 ppm a.i. Surf. C | 4 hour | 6.4 | −0.2 |
|  | 24 hour | 6.6 | 0.2 |
| 15 ppm a.i. Surf. B | 4 hour | 7.5 | −1.3 |
|  | 24 hour | 6.5 | 0.3 |
| 15 ppm a.i. Surf. A | 4 hour | 6.3 | −0.1 |
|  | 24 hour | 6.8 | 0.0 |
| 1.5 ppm a.i. CMIT/MIT and 15 ppm ai. Surf. C | 4 hour | 2.8 | 3.4 |
|  | 24 hour | 4.5 | 2.2 |
| 1.5 ppm a.i. CMIT/MIT and 15 ppm ai. Surf. B | 4 hour | 3.0 | 3.3 |
|  | 24 hour | 4.4 | 2.4 |
| 1.5 ppm a.i. CMIT/MIT and 15 ppm ai. Surf. A | 4 hour | 3.6 | 2.6 |
|  | 24 hour | 4.4 | 2.4 |

Example 7

CMIT/MIT biocide (1.5 ppm active ingredient; a.i.) alone showed a 1.2 log reduction at 4 hours and a 2.2 log reduction at 24 hours for control of bacterial biofouling compared to the untreated control.

The combinations of 1.5 ppm CMIT/MIT with 5 ppm Surf. B and Surf. A (1:3.3 wt % ratio) all showed improved bacterial biofilm control compared to the CMIT/MIT treatment alone.

In this test, Surf. C showed no improvement in the bacterial control with CMIT/MIT, but Surf. A showed no viable bacteria on the 24 hour treated biofilm samples. Therefore, Surf. A and B improved the control of bacterial biofilm growth by CMIT/MIT biocide.

| Treatment | Sample Time | Biofilm Log Growth Cells/$cm^2$ | Log Reduction vs Untreated Control |
|---|---|---|---|
| Untreated Control | 4 hour | 6.4 | 0.0 |
|  | 24 hour | 6.9 | 0.0 |
| 1.5 ppm a.i. CMIT/MIT | 4 hour | 5.2 | 1.2 |
|  | 24 hour | 4.7 | 2.2 |

-continued

| Treatment | Sample Time | Biofilm Log Growth Cells/cm$^2$ | Log Reduction vs Untreated Control |
|---|---|---|---|
| 1.5 ppm a.i. CMIT/MIT + 5 ppm ai. Surf. C | 4 hour 24 hour | 4.9 4.5 | 1.4 2.4 |
| 1.5 ppm a.i. CMIT/MIT + 5 ppm ai. Surf. B | 4 hour 24 hour | 3.6 4.0 | 2.8 2.9 |
| 1.5 ppm a.i. CMIT/MIT + 5 ppm ai. Surf. A | 4 hour 24 hour | 3.7 1.8* | 2.7 ≥5.1 |

*Limit of detection = no viable cells recovered

Example 8

CMIT/MIT biocide (1.5 ppm active ingredient; a.i.) alone showed a 2.3 log reduction at 4 hours and a 2.5 log reduction at 24 hours for control of bacterial biofouling compared to the untreated control.

Surf. A (5 ppm active) with CMIT/MIT (1.5 ppm) (1:3.3 wt % ratio of biocide:surfactant) showed improved bacterial biofilm control compared to the CMIT/MIT treatment alone.

| Treatment | Sample Time | Biofilm Log Growth Cells/cm$^2$ | Log Reduction vs Untreated Control |
|---|---|---|---|
| Untreated Control | 4 hour 24 hour | 4.5 5.3 | 0.0 0.0 |
| 1.5 ppm a.i CMIT/MIT | 4 hour 24 hour | 2.2 2.8 | 2.3 2.5 |
| 1.5 ppm a.i. CMIT/MIT + 5 ppm ai. Surf. A | 4 hour 24 hour | 1.5 2.1 | 3.0 3.2 |

*Limit of detection = no viable cells recovered

Example 9

CMIT/MIT biocide alone at 1.5 and 3 ppm active showed a 1.4 to 2.3 log reduction in bacterial biofilm growth after 4 to 24 hours compared to the untreated control. The combination of CMIT/MIT with Surf. A (1:3.3 wt % ratio) showed improved bacterial biofilm control compared to the CMIT/MIT treatment alone after 24 hours contact. No bacterial control was seen with only 50 ppm active Surf. A. Therefore, this surfactant improved the control of bacterial biofilm growth by CMIT/MIT biocide (within normal dose ranges for this biocide), yet showed no control when tested alone.

| Treatment | Sample Time | Biofilm Log Growth Cells/cm$^2$ | Log Reduction vs Untreated Control |
|---|---|---|---|
| Untreated Control | 4 hr 24 hr | 6.6 6.9 | 0.0 0.0 |
| 1.5 ppm a.i. CMIT/MIT | 4 hr 24 hr | 4.5 5.5 | 2.0 1.4 |
| 3 ppm ai CMIT/MIT | 4 hr 24 hr | 5.1 4.7 | 1.5 2.3 |
| 1.5 ppm a.i. CMIT/MIT + 5 ppm ai. Surf. A | 4 hr 24 hr | 5.2 4.5 | 1.4 2.4 |
| 3 ppm a.i. CMIT/MIT + 10 ppm ai. Surf. A | 4 hr 24 hr | 5.4 2.9 | 1.1 4.0 |
| 50 ppm Surf. A | 4 hr 24 hr | 7.4 6.8 | −0.9 0.2 |

Example 10

Treatments were evaluated in a CDC Biofilm Reactor against a mixed environmental sample which included *Legionella* bacteria, as described above under Materials and Methods.

| Treatment | Sample Time | *Legionella* Biofilm Log Growth Cells/cm$^2$ | *Legionella* Log Reduction vs Untreated Control |
|---|---|---|---|
| 1.5 ppm a.i CMIT/MIT | 0 hour 24 hour 72 Hour 96 Hour 7 Days | 2.72 2.66 2.57 0 0 | 0 0.06 0.15 2.27 2.72 |
| 1.5 ppm a.i. CMIT/MIT + 5 ppm ai. Surf. A | 0 hour 24 hour 72 Hour 96 Hour 7 Days | 2.81 1.6 1.6 0 2.2 | 0 1.21 1.21 2.81 0.61 |

Example 11

Evaluation of Lower Surfactant:CMIT/MIT Ratios

A series of samples were prepared with four different surfactants (TERGITOL L-61, TERGITOL L-64, Surfactant B, and Surfactant A), each at 3% or 1.5% of the formulation. Each formulation contained approximately 11% of KATHON™ CF 1400 biocide, for a final active ingredient concentration of 1.5% CMIT/MIT. The remainder of the formulation was deionized water. Control samples were made by adding water in the place of surfactant. The unstabilized control was made from KATHON™ WT and did not contain any of the iodine that stabilized the other formulations.

Each sample was analyzed for the level of active ingredient in KATHON™ CF 1400 (CMIT and MIT) at time zero and weekly thereafter for 4 weeks. The total active ingredient level is the sum of the concentration of CMIT and MIT. The samples were analyzed by high pressure liquid chromatography (HPLC).

Samples were prepared and analyzed for CMIT and MIT levels at time zero to ensure that all samples were dosed correctly. After analysis, the samples were split into three vials—one for heat aging at 25° C., one for heat aging at 40° C., and one for heat aging at 55° C.

TABLE 1

Active Ingredient analysis for CMIT/MIT and surfactant samples at time 0.

| Sample | CMIT | MIT | Total AI | AI Ratio | Mg(NO$_3$)$_2$ |
|---|---|---|---|---|---|
| CMIT/MIT (no stabilizer) | 1.137 | 0.376 | 1.51 | 75.2 | 2.3 |
| CMIT/MIT (with stabilizer) | 1.195 | 0.394 | 1.59 | 75.2 | 2.3 |
| CMIT/MIT + Surf. B- 1.5% | 1.150 | 0.379 | 1.53 | 75.2 | 2.3 |
| CMIT/MIT + Surf. B- 3.0% | 1.120 | 0.369 | 1.49 | 75.2 | 2.3 |
| CMIT/MIT + Surf. A- 1.5% | 1.151 | 0.379 | 1.53 | 75.2 | 2.3 |
| CMIT/MIT + Surf. A- 3.0% | 1.146 | 0.377 | 1.52 | 75.3 | 2.3 |
| CMIT/MIT + TERGITOL L-61-1.5% | 1.201 | 0.395 | 1.60 | 75.3 | 2.3 |
| CMIT/MIT + TERGITOL L-61-3.0% | 1.190 | 0.392 | 1.58 | 75.2 | 2.3 |
| CMIT/MIT + TERGITOL L-64-1.5% | 1.144 | 0.376 | 1.52 | 75.3 | 2.3 |
| CMIT/MIT + TERGITOL L-64-3.0% | 1.146 | 0.378 | 1.52 | 75.2 | 2.3 |

Samples were then analyzed weekly for four weeks to determine stability after heat aging.

TABLE 2

Active Ingredient analysis for CMIT/MIT and surfactant samples after heat aging for one week.

| Temp (° C.) | Sample | CMIT | MIT | Total AI | AI Ratio | Mg(NO$_3$)$_2$ |
|---|---|---|---|---|---|---|
| 25 | CMIT/MIT (no stabilizer) | 1.145 | 0.378 | 1.52 | 75.2 | 2.3 |
| 25 | CMIT/MIT (with stabilizer) | 1.204 | 0.399 | 1.60 | 75.1 | 2.4 |
| 25 | CMIT/MIT + Surf. B- 1.5% | 1.167 | 0.387 | 1.55 | 75.1 | 2.3 |
| 25 | CMIT/MIT + Surf. B- 3.0% | 1.135 | 0.375 | 1.51 | 75.2 | 2.3 |
| 25 | CMIT/MIT + Surf. A- 1.5% | 1.175 | 0.388 | 1.56 | 75.2 | 2.4 |
| 25 | CMIT/MIT + Surf. A- 3.0% | 1.184 | 0.392 | 1.58 | 75.1 | 2.4 |
| 25 | CMIT/MIT + TERGITOL L-61-1.5% | | | Cloudy | | |
| 25 | CMIT/MIT + TERGITOL L-61-3.0% | | | Cloudy | | |
| 25 | CMIT/MIT + TERGITOL L-64-1.5% | 1.159 | 0.384 | 1.54 | 75.1 | 2.4 |
| 25 | CMIT/MIT + TERGITOL L-64-3.0% | 1.152 | 0.381 | 1.53 | 75.1 | 2.3 |
| 40 | CMIT/MIT (no stabilizer) | 1.092 | 0.376 | 1.47 | 74.4 | 2.3 |
| 40 | CMIT/MIT (with stabilizer) | 1.174 | 0.389 | 1.56 | 75.1 | 2.4 |
| 40 | CMIT/MIT + Surf. B- 1.5% | 1.174 | 0.388 | 1.56 | 75.1 | 2.4 |
| 40 | CMIT/MIT + Surf. B- 3.0% | 1.126 | 0.373 | 1.50 | 75.1 | 2.3 |
| 40 | CMIT/MIT + Surf. A- 1.5% | 1.202 | 0.399 | 1.60 | 75.1 | 2.4 |
| 40 | CMIT/MIT + Surf. A- 3.0% | 1.151 | 0.380 | 1.53 | 75.2 | 2.4 |
| 40 | CMIT/MIT + TERGITOL L-61-1.5% | | | Cloudy | | |
| 40 | CMIT/MIT + TERGITOL L-61-3.0% | | | Cloudy | | |
| 40 | CMIT/MIT + TERGITOL L-64-S1.5% | 1.159 | 0.384 | 1.54 | 75.1 | 2.3 |
| 40 | CMIT/MIT + TERGITOL L-64-3.0% | 1.194 | 0.395 | 1.59 | 75.1 | 2.5 |
| 55 | CMIT/MIT (no stabilizer) | 0.928 | 0.373 | 1.30 | 71.3 | 2.3 |
| 55 | CMIT/MIT (with stabilizer) | 1.191 | 0.396 | 1.59 | 75.1 | 2.4 |
| 55 | CMIT/MIT + Surf. B- 1.5% | | | Cloudy | | |
| 55 | CMIT/MIT + Surf. B- 3.0% | | | Cloudy | | |
| 55 | CMIT/MIT + Surf. A- 1.5% | 1.156 | 0.383 | 1.54 | 75.1 | 2.4 |
| 55 | CMIT/MIT + Surf. A- 3.0% | 1.238 | 0.411 | 1.65 | 75.1 | 2.5 |
| 55 | CMIT/MIT + TERGITOL L-61-1.5% | | | Cloudy | | |
| 55 | CMIT/MIT + TERGITOL L-61-3.0% | | | Cloudy | | |
| 55 | CMIT/MIT + TERGITOL L-64-1.5% | 1.181 | 0.392 | 1.57 | 75.1 | 2.4 |
| 55 | CMIT/MIT + TERGITOL L-64-3.0% | 1.160 | 0.385 | 1.55 | 75.1 | 2.4 |

Samples containing TERGITOL L-61 were cloudy after one week of heat aging. Samples containing Surf. B that were heat aged at 55° C. for one week were also cloudy.

TABLE 3

Active Ingredient analysis for CMIT/MIT and surfactant samples after heat aging for two weeks.

| Temp (° C.) | Sample | CMIT | MIT | Total AI | AI Ratio | Mg(NO$_3$)$_2$ |
|---|---|---|---|---|---|---|
| 25 | CMIT/MIT (no stabilizer) | 1.155 | 0.382 | 1.54 | 75.2 | N/A |
| 25 | CMIT/MIT (with stabilizer) | 1.225 | 0.405 | 1.63 | 75.2 | N/A |
| 25 | CMIT/MIT + Surf. B- 1.5% | 1.198 | 0.396 | 1.59 | 75.1 | N/A |
| 25 | CMIT/MIT + Surf. B- 3.0% | 1.186 | 0.392 | 1.58 | 75.2 | N/A |
| 25 | CMIT/MIT + Surf. A- 1.5% | 1.183 | 0.391 | 1.57 | 75.1 | N/A |
| 25 | CMIT/MIT + Surf. A- 3.0% | 1.233 | 0.408 | 1.64 | 75.1 | N/A |
| 25 | CMIT/MIT + TERGITOL L-61- 1.5% | | | Cloudy | | |
| 25 | CMIT/MIT + TERGITOL L-61- 3.0% | | | Cloudy | | |
| 25 | CMIT/MIT + TERGITOL L-64- 1.5% | 1.208 | 0.399 | 1.61 | 75.2 | N/A |
| 25 | CMIT/MIT + TERGITOL L-64- 3.0% | 1.176 | 0.389 | 1.57 | 75.2 | N/A |
| 40 | CMIT/MIT (no stabilizer) | 1.000 | 0.381 | 1.38 | 72.4 | N/A |
| 40 | CMIT/MIT (with stabilizer) | 1.222 | 0.404 | 1.63 | 75.1 | N/A |
| 40 | CMIT/MIT + Surf. B- 1.5% | 1.205 | 0.400 | 1.60 | 75.1 | N/A |
| 40 | CMIT/MIT + Surf. B- 3.0% | 1.191 | 0.393 | 1.58 | 75.2 | N/A |
| 40 | CMIT/MIT + Surf. A- 1.5% | 1.215 | 0.402 | 1.62 | 75.1 | N/A |
| 40 | CMIT/MIT + Surf. A- 3.0% | 1.182 | 0.390 | 1.57 | 75.2 | N/A |
| 40 | CMIT/MIT + TERGITOL L-61- 1.5% | | | Cloudy | | |
| 40 | CMIT/MIT + TERGITOL L-61- 3.0% | | | Cloudy | | |
| 40 | CMIT/MIT + TERGITOL L-64- 1.5% | 1.173 | 0.388 | 1.56 | 75.1 | N/A |
| 40 | CMIT/MIT + TERGITOL L-64- 3.0% | 1.242 | 0.410 | 1.65 | 75.2 | N/A |
| 55 | CMIT/MIT (no stabilizer) | 0.708 | 0.382 | 1.09 | 64.9 | N/A |
| 55 | CMIT/MIT (with stabilizer) | 1.237 | 0.409 | 1.65 | 75.1 | N/A |
| 55 | CMIT/MIT + Surf. B- 1.5% | | | Cloudy | | |
| 55 | CMIT/MIT + Surf. B- 3.0% | | | Cloudy | | |
| 55 | CMIT/MIT + Surf. A- 1.5% | 1.243 | 0.413 | 1.66 | 75.1 | N/A |

TABLE 3-continued

Active Ingredient analysis for CMIT/MIT and surfactant samples after heat aging for two weeks.

| Temp (° C.) | Sample | CMIT | MIT | Total AI | AI Ratio | Mg(NO$_3$)$_2$ |
|---|---|---|---|---|---|---|
| 55 | CMIT/MIT + Surf. A- 3.0% | 1.278 | 0.424 | 1.70 | 75.1 | N/A |
| 55 | CMIT/MIT + TERGITOL L-61- 1.5% | | | Cloudy | | |
| 55 | CMIT/MIT + TERGITOL L-61- 3.0% | | | Cloudy | | |
| 55 | CMIT/MIT + TERGITOL L-64- 1.5% | 1.244 | 0.413 | 1.66 | 75.1 | N/A |
| 55 | CMIT/MIT + TERGITOL L-64- 3.0% | 1.208 | 0.400 | 1.61 | 75.1 | N/A |

The level of Mg(NO$_3$)$_2$ could not be analyzed due to broad peaks at the two week time point.

TABLE 4

Active Ingredient analysis for CMIT/MIT and surfactant samples after heat aging for three weeks.

| Temp (° C.) | Sample | CMIT | MIT | Total AI | AI Ratio | Mg(NO$_3$)$_2$ |
|---|---|---|---|---|---|---|
| 25 | CMIT/MIT (no stabilizer) | 1.155 | 0.383 | 1.54 | 75.1 | 2.4 |
| 25 | CMIT/MIT (with stabilizer) | 1.231 | 0.409 | 1.64 | 75.1 | 2.5 |
| 25 | CMIT/MIT + Surf. B- 1.5% | 1.188 | 0.394 | 1.58 | 75.1 | 2.4 |
| 25 | CMIT/MIT + Surf. B- 3.0% | 1.153 | 0.382 | 1.54 | 75.1 | 2.4 |
| 25 | CMIT/MIT + Surf. A- 1.5% | 1.200 | 0.397 | 1.60 | 75.1 | 2.4 |
| 25 | CMIT/MIT + Surf. A- 3.0% | 1.199 | 0.399 | 1.60 | 75.1 | 2.5 |
| 25 | CMIT/MIT + TERGITOL L-61- 1.5% | | | Cloudy | | |
| 25 | CMIT/MIT + TERGITOL L-61- 3.0% | | | Cloudy | | |
| 25 | CMIT/MIT + TERGITOL L-64- 1.5% | 1.182 | 0.392 | 1.57 | 75.1 | 2.4 |
| 25 | CMIT/MIT + TERGITOL L-64- 3.0% | 1.177 | 0.392 | 1.57 | 75.0 | 2.4 |
| 40 | CMIT/MIT (no stabilizer) | 0.804 | 0.374 | 1.18 | 68.2 | 2.3 |
| 40 | CMIT/MIT (with stabilizer) | 1.203 | 0.397 | 1.60 | 75.2 | 2.5 |
| 40 | CMIT/MIT + Surf. B- 1.5% | 1.207 | 0.402 | 1.61 | 75.0 | 2.5 |
| 40 | CMIT/MIT + Surf. B- 3.0% | 1.166 | 0.386 | 1.55 | 75.1 | 2.4 |
| 40 | CMIT/MIT + Surf. A- 1.5% | 1.235 | 0.411 | 1.65 | 75.0 | 2.5 |
| 40 | CMIT/MIT + Surf. A- 3.0% | 1.159 | 0.384 | 1.54 | 75.1 | 2.4 |
| 40 | CMIT/MIT + TERGITOL L-61- 1.5% | | | Cloudy | | |
| 40 | CMIT/MIT + TERGITOL L-61- 3.0% | | | Cloudy | | |
| 40 | CMIT/MIT + TERGITOL L-64- 1.5% | 1.206 | 0.401 | 1.61 | 75.0 | 2.5 |
| 40 | CMIT/MIT + TERGITOL L-64- 3.0% | 1.247 | 0.413 | 1.66 | 75.1 | 2.6 |
| 55 | CMIT/MIT (no stabilizer) | 0.413 | 0.333 | 0.75 | 55.4 | 2.2 |
| 55 | CMIT/MIT (with stabilizer) | 1.228 | 0.405 | 1.63 | 75.2 | 2.5 |
| 55 | CMIT/MIT + Surf. B- 1.5% | | | Cloudy | | |
| 55 | CMIT/MIT + Surf. B- 3.0% | | | Cloudy | | |
| 55 | CMIT/MIT + Surf. A- 1.5% | 1.174 | 0.392 | 1.57 | 75.0 | 2.4 |
| 55 | CMIT/MIT + Surf. A- 3.0% | 1.268 | 0.424 | 1.69 | 75.0 | 2.7 |
| 55 | CMIT/MIT + TERGITOL L-61- 1.5% | | | Cloudy | | |
| 55 | CMIT/MIT + TERGITOL L-61- 3.0% | | | Cloudy | | |
| 55 | CMIT/MIT + TERGITOL L-64- 1.5% | 1.199 | 0.398 | 1.60 | 75.1 | 2.5 |
| 55 | CMIT/MIT + TERGITOL L-64- 3.0% | 1.169 | 0.386 | 1.56 | 75.2 | 2.5 |

TABLE 5

Active Ingredient analysis for CMIT/MIT and surfactant samples after heat aging for four weeks

| temp (° C.) | Sample | CMIT | MIT | total AI | AI Ratio | Mg(NO$_3$)$_2$ |
|---|---|---|---|---|---|---|
| 25 | CMIT/MIT (no stabilizer) | 1.167 | 0.385 | 1.55 | 75.2 | 2.3 |
| 25 | CMIT/MIT (with stabilizer) | 1.263 | 0.415 | 1.68 | 75.3 | 2.5 |
| 25 | CMIT/MIT + Surf. B- 1.5% | 1.180 | 0.390 | 1.57 | 75.2 | 2.4 |
| 25 | CMIT/MIT + Surf. B- 3.0% | 1.155 | 0.382 | 1.54 | 75.2 | 2.4 |
| 25 | CMIT/MIT + Surf. A- 1.5% | 1.199 | 0.396 | 1.59 | 75.2 | 2.4 |

TABLE 5-continued

Active Ingredient analysis for CMIT/MIT and surfactant samples after heat aging for four weeks

| temp (° C.) | Sample | CMIT | MIT | total AI | AI Ratio | Mg(NO3)2 |
|---|---|---|---|---|---|---|
| 25 | CMIT/MIT + Surf. A- 3.0% | 1.207 | 0.400 | 1.61 | 75.1 | 2.5 |
| 25 | CMIT/MIT + TERGITOL L-61- 1.5% | | | Cloudy | | |
| 25 | CMIT/MIT + TERGITOL L-61- 3.0% | | | Cloudy | | |
| 25 | CMIT/MIT + TERGITOL L-64- 1.5% | 1.202 | 0.395 | 1.60 | 75.3 | 2.4 |
| 25 | CMIT/MIT + TERGITOL L-64- 3.0% | 1.173 | 0.389 | 1.56 | 75.1 | 2.4 |
| 40 | CMIT/MIT (no stabilizer) | 0.710 | 0.374 | 1.08 | 65.5 | 2.3 |
| 40 | CMIT/MIT (with stabilizer) | 1.198 | 0.394 | 1.59 | 75.2 | 2.4 |
| 40 | CMIT/MIT + Surf. B- 1.5% | 1.202 | 0.397 | 1.60 | 75.2 | 2.5 |
| 40 | CMIT/MIT + Surf. B- 3.0% | 1.170 | 0.386 | 1.56 | 75.2 | 2.4 |
| 40 | CMIT/MIT + Surf. A- 1.5% | 1.236 | 0.409 | 1.65 | 75.1 | 2.5 |
| 40 | CMIT/MIT + Surf. A- 3.0% | 1.159 | 0.381 | 1.54 | 75.3 | 2.4 |
| 40 | CMIT/MIT + TERGITOL L-61- 1.5% | | | Cloudy | | |
| 40 | CMIT/MIT + TERGITOL L-61- 3.0% | | | Cloudy | | |
| 40 | CMIT/MIT + TERGITOL L-64- 1.5% | 1.191 | 0.392 | 1.58 | 75.2 | 2.4 |
| 40 | CMIT/MIT + TERGITOL L-64- 3.0% | 1.221 | 0.402 | 1.62 | 75.2 | 2.5 |
| 55 | CMIT/MIT (no stabilizer) | 0.291 | 0.313 | 0.60 | 48.2 | 2.2 |
| 55 | CMIT/MIT (with stabilizer) | 1.204 | 0.398 | 1.60 | 75.2 | 2.4 |
| 55 | CMIT/MIT + Surf. B- 1.5% | | | Cloudy | | |
| 55 | CMIT/MIT + Surf. B- 3.0% | | | Cloudy | | |
| 55 | CMIT/MIT + Surf. A- 1.5% | 1.185 | 0.392 | 1.58 | 75.2 | 2.4 |
| 55 | CMIT/MIT + Surf. A- 3.0% | 1.251 | 0.414 | 1.66 | 75.2 | 2.7 |
| 55 | CMIT/MIT + TERGITOL L-61- 1.5% | | | Cloudy | | |
| 55 | CMIT/MIT + TERGITOL L-61- 3.0% | | | Cloudy | | |
| 55 | CMIT/MIT + TERGITOL L-64- 1.5% | 1.201 | 0.398 | 1.60 | 75.1 | 2.5 |
| 55 | CMIT/MIT + TERGITOL L-64- 3.0% | 1.157 | 0.382 | 1.54 | 75.2 | 2.5 |

After heat aging for four weeks, all samples that were not cloudy remained fairly stable, except for the unstabilized CMIT/MIT samples.

TABLE 6

Percent of the total active ingredient remaining after heat aging in each of the CMIT/MIT and surfactant blends.

| Sample | Temp (° C.) | t = 0 | t = 1 week | t = 2 weeks | t = 3 weeks | t = 4 weeks |
|---|---|---|---|---|---|---|
| CMIT/MIT (no stabilizer) | 25 | 100 | 101 | 102 | 102 | 103 |
| CMIT/MIT (with stabilizer) | 25 | 100 | 101 | 108 | 103 | 106 |
| CMIT/MIT + Surf. B- 1.5% | 25 | 100 | 102 | 105 | 104 | 103 |
| CMIT/MIT + Surf. B- 3.0% | 25 | 100 | 101 | 104 | 103 | 103 |
| CMIT/MIT + Surf. A- 1.5% | 25 | 100 | 102 | 104 | 104 | 104 |
| CMIT/MIT + Surf. A- 3.0% | 25 | 100 | 104 | 108 | 105 | 106 |
| CMIT/MIT + TERGITOL L-61- 1.5% | 25 | | | Cloudy | | |
| CMIT/MIT + TERGITOL L-61- 3.0% | 25 | | | Cloudy | | |
| CMIT/MIT + TERGITOL L-64- 1.5% | 25 | 100 | 102 | 106 | 104 | 105 |
| CMIT/MIT + TERGITOL L-64- 3.0% | 25 | 100 | 101 | 103 | 103 | 103 |
| CMIT/MIT (no stabilizer) | 40 | 100 | 97 | 91 | 78 | 72 |
| CMIT/MIT (with stabilizer) | 40 | 100 | 98 | 107 | 101 | 100 |
| CMIT/MIT + Surf. B- 1.5% | 40 | 100 | 102 | 106 | 105 | 105 |
| CMIT/MIT + Surf. B- 3.0% | 40 | 100 | 101 | 105 | 104 | 104 |
| CMIT/MIT + Surf. A- 1.5% | 40 | 100 | 105 | 107 | 108 | 108 |
| CMIT/MIT + Surf. A- 3.0% | 40 | 100 | 101 | 104 | 101 | 101 |
| CMIT/MIT + TERGITOL L-61- 1.5% | 40 | | | Cloudy | | |
| CMIT/MIT + TERGITOL L-61- 3.0% | 40 | | | Cloudy | | |
| CMIT/MIT + TERGITOL L-64- 1.5% | 40 | 100 | 102 | 103 | 106 | 104 |
| CMIT/MIT + TERGITOL L-64- 3.0% | 40 | 100 | 104 | 109 | 109 | 107 |
| CMIT/MIT (no stabilizer) | 55 | 100 | 86 | 72 | 49 | 40 |
| CMIT/MIT (with stabilizer) | 55 | 100 | 100 | 109 | 103 | 101 |
| CMIT/MIT + Surf. B- 1.5% | 55 | 100 | | Cloudy | | |
| CMIT/MIT + Surf. B- 3.0% | 55 | 100 | | Cloudy | | |
| CMIT/MIT + Surf. A- 1.5% | 55 | 100 | 101 | 109 | 102 | 103 |

TABLE 6-continued

Percent of the total active ingredient remaining after heat aging in each of the CMIT/MIT and surfactant blends.

| Sample | Temp (° C.) | t = 0 | Percent Remaining | | | |
|---|---|---|---|---|---|---|
| | | | t = 1 week | t = 2 weeks | t = 3 weeks | t = 4 weeks |
| CMIT/MIT + Surf. A- 3.0% | 55 | 100 | 108 | 113 | 111 | 109 |
| CMIT/MIT + TERGITOL L-61- 1.5% | 55 | | | Cloudy | | |
| CMIT/MIT + TERGITOL L-61- 3.0% | 55 | | | Cloudy | | |
| CMIT/MIT + TERGITOL L-64- 1.5% | 55 | 100 | 103 | 110 | 105 | 105 |
| CMIT/MIT + TERGITOL L-64- 3.0% | 55 | 100 | 101 | 106 | 102 | 101 |

Some of the values for percent remaining are higher than the initial values recorded for the samples. This is likely because some of the water evaporated during the heat aging. In order to provide a more accurate picture of the stability of the samples, the total active ingredient value was normalized to the $Mg(NO_3)_2$ concentration before being normalized to the starting concentration of CMIT and MIT. Table 7 describes these results.

TABLE 7

Percentage of the active ingredients remaining in each sample after normalizing to $Mg(NO_3)_2$ to account for evaporation during the heat aging process.

| Sample | Temp (° C.) | t = 0 | Percent Remaining | | |
|---|---|---|---|---|---|
| | | | t = 1 week | t = 3 weeks | t = 4 weeks |
| CMIT/MIT (no stabilizer) | 25 | 100 | 101 | 99 | 100 |
| CMIT/MIT (with stabilizer) | 25 | 100 | 96 | 94 | 95 |
| CMIT/MIT + Surf. B- 1.5% | 25 | 100 | 99 | 98 | 99 |
| CMIT/MIT + Surf. B- 3.0% | 25 | 100 | 102 | 100 | 100 |
| CMIT/MIT + Surf. A- 1.5% | 25 | 100 | 97 | 98 | 99 |
| CMIT/MIT + Surf. A- 3.0% | 25 | 100 | 99 | 98 | 98 |
| CMIT/MIT + TERGITOL L-61- 1.5% | 25 | | Cloudy | | |
| CMIT/MIT + TERGITOL L-61- 3.0% | 25 | | Cloudy | | |
| CMIT/MIT + TERGITOL L-64- 1.5% | 25 | 100 | 99 | 98 | 99 |
| CMIT/MIT + TERGITOL L-64- 3.0% | 25 | 100 | 99 | 97 | 99 |
| CMIT/MIT (no stabilizer) | 40 | 100 | 97 | 77 | 71 |
| CMIT/MIT (with stabilizer) | 40 | 100 | 95 | 92 | 95 |
| CMIT/MIT + Surf. B- 1.5% | 40 | 100 | 99 | 97 | 98 |
| CMIT/MIT + Surf. B- 3.0% | 40 | 100 | 100 | 98 | 100 |
| CMIT/MIT + Surf. A- 1.5% | 40 | 100 | 98 | 98 | 99 |
| CMIT/MIT + Surf. A- 3.0% | 40 | 100 | 96 | 98 | 98 |
| CMIT/MIT + TERGITOL L-61- 1.5% | 40 | | Cloudy | | |
| CMIT/MIT + TERGITOL L-61- 3.0% | 40 | | Cloudy | | |
| CMIT/MIT + TERGITOL L-64- 1.5% | 40 | 100 | 99 | 93 | 94 |
| CMIT/MIT + TERGITOL L-64- 3.0% | 40 | 100 | 97 | 93 | 93 |
| CMIT/MIT (no stabilizer) | 55 | 100 | 85 | 51 | 42 |
| CMIT/MIT (with stabilizer) | 55 | 100 | 94 | 94 | 95 |
| CMIT/MIT + Surf. B- 1.5% | 55 | 100 | Cloudy | | |
| CMIT/MIT + Surf. B- 3.0% | 55 | 100 | Cloudy | | |
| CMIT/MIT + Surf. A- 1.5% | 55 | 100 | 97 | 97 | 97 |
| CMIT/MIT + Surf. A- 3.0% | 55 | 100 | 98 | 93 | 94 |
| CMIT/MIT + TERGITOL L-61- 1.5% | 55 | | Cloudy | | |
| CMIT/MIT + TERGITOL L-61- 3.0% | 55 | | Cloudy | | |
| CMIT/MIT + TERGITOL L-64- 1.5% | 55 | 100 | 98 | 96 | 94 |
| CMIT/MIT + TERGITOL L-64- 3.0% | 55 | 100 | 98 | 95 | 94 |

All of the samples that remained clear were stable for one month at 55° C., except for the unstabilized CMIT/MIT samples. The percent remaining was not calculated for t=2 weeks because the $Mg(NO_3)_2$ levels were not accurately calculated for that time point.

Example 12

Efficacy of 1:1 CMIT/MIT:Surfactant Combinations

Media
Trypticase Soy Broth Agar (TSBA)
  Weigh 30 g Trypticase Soy Broth (Difco) and 15 g Agar (Difco) into a 2 liter flask.
  Add 1000 ml deionized water.
  Autoclave at 121° C. for 20 minutes.
  Pour 25 mls of TSBA into sterile plates (VWR)
Potato Dextrose Broth (PDB)
  Weigh 24 g Potato Dextrose Broth (Difco) into a 2 liter flask.

Add 1000 ml deionized water.
Mix thoroughly, boil for 1 minute
Autoclave at 121° C. for 20 minutes.
Sabouraud Dextrose Agar (SDA)
  Weigh 195 g Sabouraud Dextrose Agar (Difco) into a 2 liter flask.
  Add 1000 ml deionized water.
  Mix thoroughly, boil for 1 minute
  Autoclave at 121° C. for 20 minutes.
  Let cool in a waterbath, then add 100 µl gentomycin (Sigma) and 100 µl
  Streptomycin (Sigma) to media
  Pour 25 mls of SDA into sterile plates (VWR)
Trypticase Soy Broth (TSB)
  Weigh 30 g Trypticase Soy Broth (Difco) into a 2 liter flask.
  Add 1000 ml deionized water.
  Autoclave at 121° C. for 20 minutes.
Alga-Gro Concentrated Medium
  Weigh 0.3 g Agar (Difco) into 100 ml flask.
  Add 60 ml of deionized water.
  Autoclave at 121° C. for 20 minutes.
  Allow to cool.
  Add 1.2 ml Alga-Gro Concentrated Medium (Carolina Biological Supply)
Methods
High Resolution Minimum Inhibitory Concentration Evaluations
Microorganisms The following microorganisms tested were obtained from the American Type Culture Collection (ATCC; Manassas, Va., USA).

| Strain | Source |
| --- | --- |
| Pseudomonas aeruginosa | ATCC 15442 |
| Staphylococcus aureus | ATCC 6538 |
| Candida albicans | ATCC 2091 |
| Sacchromyces cerevisiae | ATCC 18824 |
| Chlorella sp. | ATCC 30582/UTEX 26 |

Culture
Maintenance

Bacteria were grown on TSBA at 30° C. for 48 hours. Fungi were grown on SDA at 25° C. for 48 hours. Each plate was washed with approximately 5 mL of phosphate buffer, pH 7.2. The culture suspension was mixed with an equal volume of sterile 50% glycerol. The resulting suspension was dispensed in 1 mL portions into 2 mL cryovials and stored at −70° C. Microorganisms were recovered from frozen croyovials prior to testing. Bacteria were grown on TSBA at 30° C. for 48 hours. Fungi were grown on SDA at 30° C. for 48 hours.

Algae were grown and maintained in a liquid culture media (Bold's 3N Medium). Algae was collected, centrifuged at 600 g for 6 minutes and resuspended in culture media. Algae species were mixed and 100 uL were placed onto biocide containing agar plates. Plates were incubated under constant light at 30° C.

For the preparation of the algal medium: 20 g of Bacto agar was added to 980 mL dH$_2$O, autoclaved sterilized at 121° C. for 30 minutes, placed into a 50° C. water bath before 20 mL of Bold's 3N (50× stock) was added to each liter. Portions of the agar were aspectically transferred to sterile flasks where desired amounts of biocide were added before agar was poured into petri plates. Petri plates were filled with ~20 ml of the final algal media containing the biocide.

Instruments and Equipment Used

| Instrument/Equipment | Brand/Model |
| --- | --- |
| Analytical balance | Sartorius |
| Incubator | Lab-Line Instruments, Inc. |
| Autoclave | Amsco |
| UV/VIS Spectrometer | Spectronic 20 GENESYS |

The lowest concentration of microbicides required to inhibit bacteria and fungi was determined by a high resolution minimum inhibitory concentration (HRMIC) test. Varying amounts of each microbicide were added to media in a 96-well microtiter plate. The media used for the HRMIC tests was Trypticase Soy Broth (TSB) for bacteria and Potato Dextrose Broth (PDB) for fungi. Stationary phase bacteria were grown overnight at 30° C. in a rotary shaking incubator (125 reciprocations per minute) in TSB. Phosphate buffer suspensions of fungi were prepared and diluted into PDB. The overnight cultures were calibrated to an OD value of 0.40 to ensure a starting bacteria suspension of ~$1.0\times10^8$ cfu/mL. Appropriate dilutions were performed in the appropriate test media and inoculated into the test to provide approximately $10^6$ CFU/mL in each well for bacteria or $10^5$ CFU/mL in each well for fungi. Triplicate cell suspensions were prepared for all organisms. The microtiter plates were incubated at 30° C. for 24 hours for bacteria and 25° C. for seven days for fungi and were then checked for the presence or absence of microbial growth by observing the turbidity in each well. Algae were grown and maintained in a liquid culture media (Bold's 3N Medium). Algae was collected, centrifuged at 600 g for 6 minutes, and resuspended in culture media. Algae species were mixed and 100 uL were placed onto biocide containing agar plates. Plates were incubated under constant light at 30° C. After incubation, the presence of growth on biocide containing agar plates were checked visually and compared against control plates. The concentration of compound in the first microtiter well demonstrating no growth was the minimum inhibitory concentration (MIC) for the microbicide. The high resolution MIC test is more accurate than a typical two-fold MIC test because the end points are closely spaced, allowing for greater differentiation between the compounds tested. The MIC value for each microbicide was determined from the average of three different inoculum tests—with each inoculum run in triplicates—for each of the bacteria, fungi, and algae.

Concentration (ppm Active Ingredient) of CMIT/MIT in the HRMIC Test

| 1.5% CMIT/MIT | | | | 1.5% CMIT/MIT + Surf. A | | | |
| --- | --- | --- | --- | --- | --- | --- | --- |
| 1 | 2 | 3 | 4 | 5 | 6 | 7 | 8 |
| 15.0 | 1.50 | 0.150 | 0.015 | 15 + 15 | 1.50 + 1.50 | 0.15 + 0.15 | 0.015 + 0.015 |
| 12.0 | 1.20 | 0.120 | 0.012 | 12 + 12 | 1.20 + 1.20 | 0.12 + 0.12 | 0.012 + 0.012 |
| 9.0 | 0.90 | 0.090 | 0.009 | 9 + 9 | 0.90 + 0.90 | 0.09 + 0.09 | 0.009 + 0.009 |
| 7.5 | 0.75 | 0.075 | 0.0075 | 7.5 + 7.5 | 0.75 + 0.75 | 0.075 + 0.075 | 0.0075 + 0.0075 |
| 6.0 | 0.60 | 0.060 | 0.0060 | 6 + 6 | 0.60 + 0.60 | 0.06 + 0.06 | 0.006 + 0.006 |

-continued

| 1.5% CMIT/MIT | | | | 1.5% CMIT/MIT + Surf. A | | | |
|---|---|---|---|---|---|---|---|
| 1 | 2 | 3 | 4 | 5 | 6 | 7 | 8 |
| 4.5 | 0.45 | 0.045 | 0.0045 | 4.5 + 4.5 | 0.45 + 0.45 | 0.045 + 0.045 | 0.0045 + 0.0045 |
| 3.0 | 0.30 | 0.030 | 0.0030 | 3 + 3 | 0.30 + 0.30 | 0.03 + 0.03 | 0.003 + 0.003 |
| 0.0 | 0.00 | 0.00 | 0.00 | 0.00 | 0.00 | 0.00 | 0.000 |

MIC testing for the green algae strain was conducted using agar petri plates containing Bold's 3N Medium. This medium was chosen as it best supported the growth of the algae. CMIT/MIT 1.5% Microbicide and a blend of CMIT/MIT, 1.5%+Surf. A ("1:1 Mixture") were added to the agar media to provide 0.75, 1.5, 3.0, 6.0, and 12.0 ppm active ingredient.

The algal inoculum was prepared by collecting the algae, centrifuging at 600 g for 6 minutes and resuspending in culture media. A 100 μL amount of each week-old algal culture was streaked across the surface of the agar plates containing various concentrations of biocide and incubated in a lighted incubator at 30° C. The lowest concentration of biocide which inhibited the growth (visual green appearance) of the algae on the agar surface after seven days incubation at 30° C. was considered the MIC. Samples were tested in triplicate.

Antimicrobial Activity of 1.5% CMIT/MIT+1.5% Surf. A ("1:1 Mixture")

The MIC values of the 1:1 Mixture and 1.5% CMIT/MIT were determined against mixtures of bacteria (Experiment 1, 2 and 3) or fungi (4,5, and 6) using a high resolution MIC method in TSB or PDB as described earlier. The MIC values of 1:1 Mixture and 1.5% CMIT/MIT were determined against algae using an agar plate MIC method in Bacto agar as described earlier. The results indicate that the 1:1 Mixture and 1.5% CMIT/MIT is a highly effective microbicide that inhibits microbial growth at low levels. In addition, the MIC of 1:1 mixture is similar to the MIC of 1.5% CMIT/MIT. The ppm a.i. in the MIC studies refer to the amount of CMIT/MIT present in test condition.

Experiment 1: MIC of 1:1 Mixture and 1.5% CMIT/MIT vs. Bacteria

| | 1:1 Mixture | | 1.5% CMIT/MIT | |
|---|---|---|---|---|
| Microorganisms | MIC (ppm a.i) | SD (+/−) | MIC (ppm a.i) | SD (+/−) |
| Pseudomonas aeruginosa (ATCC 15442) and Staphylococcus aureus (ATCC 6538) | 0.3 | 0 | 3 | 0 |

Experiment 2: MIC of 1:1 Mixture and 1.5% CMIT/MIT vs. Bacteria

| | 1:1 Mixture | | 1.5% CMIT/MIT | |
|---|---|---|---|---|
| Microorganisms | MIC (ppm a.i) | SD (+/−) | MIC (ppm a.i) | SD (+/−) |
| Pseudomonas aeruginosa (ATCC 15442) and Staphylococcus aureus (ATCC 6538) | 0.3 | 0 | 4 | 0.87 |

Experiment 3: MIC of 1:1 Mixture and 1.5% CMIT/MIT vs. Bacteria

| | 1:1 Mixture | | 1.5% CMIT/MIT | |
|---|---|---|---|---|
| Microorganisms | MIC (ppm a.i) | SD (+/−) | MIC (ppm a.i) | SD (+/−) |
| Pseudomonas aeruginosa (ATCC 15442) and Staphylococcus aureus (ATCC 6538) | 0.3 | 0 | 3.5 | 0.87 |

Experiment 1: MIC of 1:1 Mixture and 1.5% CMIT/MIT vs. Fungi

| | 1:1 Mixture | | 1.5% CMIT/MIT | |
|---|---|---|---|---|
| Microorganism | MIC (ppm a.i) | SD (+/−) | MIC (ppm a.i) | SD (+/−) |
| Candida albicans (ATCC 2091) and Saccharomyces cerevisiae (ATCC 18824) | 0.06 | 0 | 0.45 | 0 |

Experiment 2: MIC of 1:1 Mixture and 1.5% CMIT/MIT vs. Fungi

| | 1:1 Mixture | | 1.5% CMIT/MIT | |
|---|---|---|---|---|
| Microorganism | MIC (ppm a.i) | SD (+/−) | MIC (ppm a.i) | SD (+/−) |
| Candida albicans (ATCC 2091) and Saccharomyces cerevisiae (ATCC 18824) | 0.045 | 0 | 3 | 0 |

Experiment 3: MIC of 1:1 Mixture and 1.5% CMIT/MIT vs. Fungi

| | 1:1 Mixture | | 1.5% CMIT/MIT | |
|---|---|---|---|---|
| Microorganism | MIC (ppm a.i) | SD (+/−) | MIC (ppm a.i) | SD (+/−) |
| Candida albicans (ATCC 2091) and Saccharomyces cerevisiae (ATCC 18824) | 0.06 | 0 | 0.65 | 0.087 |

MIC of 1:1 Mixture and 1.5% CMIT/MIT vs. Algae
(*Chlorella vulgaris* (ATCC 30582))

| Microbicide concentration (ppm active) | Growth Observation in Replicates | | | | | |
| --- | --- | --- | --- | --- | --- | --- |
| | Replicate 1 | | Replicate 2 | | Replicate 3 | |
| | CMIT/MIT | 1:1 Mixture | CMIT/MIT | 1:1 Mixture | CMIT/MIT | 1:1 Mixture |
| 0 (control) | + | + | + | + | + | + |
| 0.75 | − | − | − | − | − | − |
| 1.5 | − | − | − | − | − | − |
| 3 | − | − | − | − | − | − |
| 6 | − | − | − | − | − | − |
| 12 | − | − | − | − | − | − |

MIC value determined for no growth on all replicates

The invention claimed is:

1. An aqueous microbicidal composition comprising: (a) 0.5-5 wt % of a mixture of 5-chloro-2-methyl-4-isothiazolin-3-one and 2-methyl-4-isothiazolin-3-one; and (b) 1-7 wt % of a nonionic surfactant having structure:

$$RO(CH_2CH(CH_3)O)_x(CH_2CH_2O)_yH$$

where R is a branched $C_6$-$C_{12}$ alkyl group, x is from 3 to 7 and y is from 5 to 12; and wherein a weight ratio of 5-chloro-2-methyl-4-isothiazolin-3-one to 2-methyl-4-isothiazolin-3-one is from 2.5:1 to 3.5:1.

2. The composition of claim 1 having from 1 to 6 wt % of said nonionic surfactant.

3. The composition of claim 2 in which R is a $C_7$-$C_9$ alkyl group, x is from 4 to 6 and y is from 5 to 7 or from 8 to 10.

4. The composition of claim 3 having from 1-3 wt % of said mixture.

5. The composition of claim 4 in which R is 2-ethylhexyl, y is 6 or 9 and a weight ratio of said nonionic surfactant to said mixture is from 5:1 to 2:1.

6. A synergistic microbicidal composition comprising: (a) a mixture of 5-chloro-2-methyl-4-isothiazolin-3-one and 2-methyl-4-isothiazolin-3-one; and (b) a nonionic surfactant with structure:

$$RO(CH_2CH(CH_3)O)_x(CH_2CH_2O)_yH$$

where R is a $C_8$ alkyl group, x is 5 and y is 6 or 9; and wherein a weight ratio of 5-chloro-2-methyl-4-isothiazolin-3-one to 2-methyl-4-isothiazolin-3-one is from 2.5:1 to 3.5:1 and a weight ratio of said mixture to said nonionic surfactant is from 1:0.5 to 1:50.

7. The synergistic microbicidal composition of claim 6 in which R is 2-ethylhexyl and y is 9; wherein a weight ratio of said mixture to said nonionic surfactant is from 1:2 to 1:50.

8. The synergistic microbicidal composition of claim 6 in which R is 2-ethylhexyl and y is 6; wherein a weight ratio of said mixture to said nonionic surfactant is from 1:0.5 to 1:10.

9. An aqueous microbicidal composition comprising: (a) a mixture of 5-chloro-2-methyl-4-isothiazolin-3-one and 2-methyl-4-isothiazolin-3-one; and (b) a nonionic surfactant having structure $$RO(CH_2CH(CH_3)O)_x(CH_2CH_2O)_yH$$

where R is a branched $C_6$-$C_{12}$ alkyl group, x is from 3 to 7 and y is from 5 to 12; wherein a weight ratio of said nonionic surfactant to said mixture is from 5:1 to 0.8:1; and wherein a weight ratio of 5-chloro-2-methyl-4-isothiazolin-3-one to 2-methyl-4-isothiazolin-3-one is from 2.5:1 to 3.5:1.

\* \* \* \* \*